US006794408B2

(12) United States Patent
Eder et al.

(10) Patent No.: US 6,794,408 B2

(45) Date of Patent: Sep. 21, 2004

(54) DRECHSLERANOL DERIVATIVES, PROCESSES FOR THEIR PREPARATION AND THEIR USE

(75) Inventors: Claudia Eder, Hofheim (DE); Michael Kurz, Hofheim (DE); Luigi Toti, Hochheim (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 10/351,773

(22) Filed: Jan. 27, 2003

(65) Prior Publication Data

US 2003/0171427 A1 Sep. 11, 2003

Related U.S. Application Data

(60) Provisional application No. 60/360,363, filed on Feb. 28, 2002.

(30) Foreign Application Priority Data

Jan. 29, 2002 (DE) ........................................ 102 03 557

(51) Int. Cl.$^7$ ...................... A61K 31/34; C07D 307/77; C12P 7/22

(52) U.S. Cl. ....................... 514/468; 252/404; 252/407; 426/545; 435/126; 549/456

(58) Field of Search ......................... 549/456; 514/468; 435/126

(56) References Cited

FOREIGN PATENT DOCUMENTS

EP 0 557 939 A1 9/1993

OTHER PUBLICATIONS

Cocker Wesley et al , The Elimination of Non–Angular Alkyl Groups in Aromatisation Reactions. Part II, Journal of the Chemical Society, 1953, pp 2355–2362.

Shatla M N et al, Studies on *Drechlsera australiensis* and Alternaria alternata leaf pot of soybean in Egypt, Monoufeia J. Agric. Res., 1980, No. 3, pp. 35–51.

Brock et al, Biology of Microorganisms, (Seventh Edition), Prentice Hall; 1994; pp. 238–247.

Keesler George A. et al., Phosphorylation and destabilization of human period I clockprotein by human casein kinase le, Neuroreport; 2000; vol. 11(5);; pp. 951–955.

Kumagae Yoshihiro et al., Human c–Jun N–terminal kinase expression and activation in the nervious system, Molecular Brain Research; 1999; vol. 67(1); pp. 10–17.

Souetre E et al., Rythmes Circadiens et Depression, Annales medico–physiologiques; 1985; vol. 143(9); pp. 845–870.

Stolp H, Microbial ecology: organisms, habitats, activities, Cambridge University Press, Cambridge, GB; 1988; p. 180.

Sugihara Naruml et al., Differences in Antioxidative Efficiency of Catechins in Various Metal–Induced Lipid Peroxidations in Cultured Hepatocytes, Journal of Health Science; 2001; vol. 47(2); pp. 99–106.

*Primary Examiner*—Bernard Dentz
(74) *Attorney, Agent, or Firm*—Lawrence Martin

(57) ABSTRACT

The present invention provides novel drechsleranol compounds of formula (I) which are formed by the microorganism *Drechslera australlensis*, ST 003360, DSM 14093, or a fungus ST 004112, DSM 14524, during fermentation. A process for their preparation, pharmaceutical compositions containing said drechsleranols their use for the treatment and/or prophylaxis of degenerative neuropathies, such as, Alzheimeu's disease, or psychiatric disorders, such as depression, sleep disturbance or seasonal affective disorder, and their use as chelating agents or antioxidants are also disclosed and claimed.

(I)

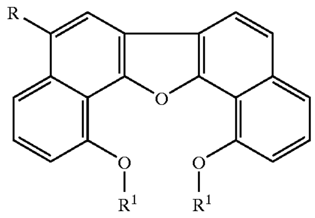

19 Claims, No Drawings

DRECHSLERANOL DERIVATIVES, PROCESSES FOR THEIR PREPARATION AND THEIR USE

This application claims the benefit of German priority document number 10203557.1, filed Jan. 29, 2002, and U.S. Provisional Application No. 60/360,363, filed Feb. 28, 2002.

BACKGROUND OF THE INVENTION

1. Field of the Invention

The present invention relates to novel compounds called drechsleranols, which are formed by the microorganism *Drechslera australlensis*, ST 003360, DSM 14003, or a fungus ST 004112, DSM 14524, which has not been determined more closely taxonomically, during fermentation, a process for the preparation of these compounds, their use as pharmaceutical compositions, and their use for the treatment and/or prophyloxis of degenerative neuropathies, for example, Alzheimer's disease, or psychiatric disorders, such as depression, sleep disturbances or seasonal affective disorder.

2. Description of the Art

Alzheimer's disease is a neuropsychiatric disorder which mainly occurs in elderly people. The disease is manifested by a multitude of symptoms which includes memory disorders, reduced perceptivity, orientation disorders, speech disorders, disorders of coordinated thought, etc. In Alzheimer's patients, characteristic neurohistological changes are found in the brain, such as, for example, deposits of "amyloid plaques" and also a degeneration of the neurofibrils in the nerve cells ("fibrillar bundles"). These neurohistological changes are characteristic, but nonspecific, since they also occur to a smaller extent in the normal aging process.

At present no causal treatment, but only symptomatic treatment, is possible for Alzheimer's disease. Currently available medicaments only delay the course of the disease, but they are not able to cure it. The group consisting of the centrally active acetylcholinesterase inhibitors (Tacrin®, Donepezil®, Rivastigmin®, Galantamin®), currently offers the most important therapeutic approach, since for the memory-relevant structures, which are impaired to a considerable extent in Alzheimer's disease, cholinergic signal transmission plays a great role. These medicaments, however, can only be employed in the early and middle stages of the disease and they act to increase the concentration of acetylcholine in the information-transmitting synapses of the brain. If there is too severe damage to the neurons, i.e. in the late stage of the disease, these compounds are no longer effective. Other substances whose use has been investigated are estrogens, nonsteroidal analgesics, antioxidants and nerve growth factors (NGF).

It is estimated that at present there are approximately one million people in the Federal Republic of Germany who are suffering from Alzheimer's disease. This figure will presumably increase still further in the next few years on account of the increasing life expectancy of the population. Novel substances for the treatment of this disorder are therefore urgently needed.

The group consisting of the c-Jun N-terminal kinases (JNKs) are protein kinases which are activated by oxidative stress. So far, it is known that only JNK-3 (in contrast to JNK-1 and JNK-2) is expressed in the neurons of the human brain. There are indications that the JNKs have an influence on cell death. This cell death (or apoptosis) is probably the causal mechanism of the death of the neurons in the brain of Alzheimer's patients (Kumagae et al., Mol. Brain Res. (1999), 67(1), 10-7). The activation of c-Jun N-terminal kinase is one step in this mechanism. Inhibition at this position in the biological cascade of apoptotic events should thus prevent apoptosis, and thereby counteract the development of Alzheimer's disease and halt the progress of the disease.

A further aspect of the present invention is the treatment and/or prohylaxis of psychiatric disorder. Circadian rhythms are generated by internal or endogenous timers (circadian clocks) which are present in a peat variety of organisms. The circadian clock is important for the maintenance of the biological rhythm. The circadian clock is self-sustaining and constant, even in total darkness, but it can be synchronized by external sign a, such as, for example, changes in the light or the temperature. The internal clock controls is the daily fluctuations of behavior, activity, food intake, the sleeping/walking cycle as well as physiological changes such as, for example, hormone secretion and change in the body temperature (Keesler at aL, Neuroreport (2000), 11(5). 951–955). Period (PER) is a central protein of this circadian clock, which is subject to daily variations with spec: to its concentration or its phosphorylation state. The phosphorylation of human PER1 (hPER1) by the enzyme human casein kinase 1 epsilon (hCK1ϵ) causes a decrease in the protein stability of hPER1. Phosphorylated hPER1 has a half life of approximately 12 hrs, whereas unphosphorylated hPER1 remains stable in cells for longer than 24 hours. Thus, modulation of hPER1 protein is clinically of importance especially in diseases which are associated with a disorder of the internal clock, such as, for example, depression (Souetre E. al., Annales medico-physiologiques, 1985, 143(9), 845–870). sleep disturbances or seasonal affective disorder. For the treatment of depression, monoamine oxidase inhibitors and inhibitors of the reuptake of noradrenaline and/or serotonin into the axoplasma (e.g. tricyclic antidepressants) are currently available; however, their exact mechanism of antidepressant action hitherto has not been clarified. With Inhibitor of hCK1ϵ, one would have available a now active principle for the treatment of psychiatric disorders, such as, for example, sleep disturbances, seasonal affective disorder and, in particular, depression.

SUMMARY OF THE INVENTION

The invention relates to a compound of the formula (I)

(I)

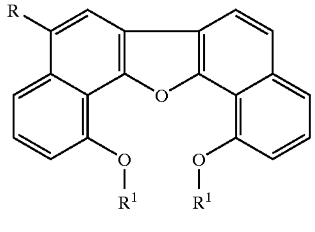

wherein:

R is H, or a group of the formula $—(CH(OR^2))_5—CH_2—OR^2$;

$R^1$ and $R^2$ independently are H, $C_1$–$C_6$-alkyl, $C_2$–$C_6$-alkenyl, $C_2$–$C_6$-alkynyl or $C_6$–$C_{10}$-aryl, wherein said $C_1$–$C_6$-alkyl, $C_2$–$C_6$-alkenyl, $C_2$–$C_6$-alkynyl or $C_6$–$C_{10}$-aryl are optionally mono- or disubstituted by —OH, =O, —O—$C_1$–$C_6$-alkyl, —O—$C_2$–$C_6$-alkenyl, $C_6$–$C_{10}$-aryl, —NH—$C_1$–$C_6$-alkyl, —NH—$C_{2-C6}$-alkenyl, —$NH_2$ or halogen, wherein said —O—$C_1$–$C_6$-alkyl, —O—$C_2$–$C_6$-alkenyl, $C_6$–$C_{10}$-aryl, —NH—$C_1$–$C_6$-alkyl and —NH—$C_2$–$C_6$-alkenyl substitutents are optionally substituted by —CN, —NH—C(O)—($C_1$–$C_6$-alkyl) or =NOH; or a stereoisomeric form thereof, or a pharmaceutically acceptable salt thereof.

DETAILED DESCRIPTION OF THE INVENTION $C_1$–$C_6$-alkyl is a straight- or branched-chain alkyl having 1 to 6 C atoms, preferably having 1 to 4 C atoms, e.g. methyl, ethyl, i-propyl, tert-butyl and hexyl.

$C_2$–$C_6$-alkenyl is a straight- or branched-chain alkenyl having 2 to 6 C atoms, which is mono-, di- or triunsaturated, e.g. allyl, crotyl, 1-propenyl, penta-1,3-dienyl and pentenyl.

$C_2$–$C_6$-alkynyl is a straight- or branched-chain alkynyl having 2 to 6 C atoms, which is mono- or di-unsaturated, e.g. propynyl, butynyl and pentynyl.

$C_6$–$C_{10}$-aryl is an aryl group having 6 to 10 C atoms, e.g. phenyl, benzyl or 1- or 2-naphthyl, which can also be optionally substituted, for example by halogen, such as chlorine, bromine, or fluorine, by alkyl having 1–4 C atoms, preferably methyl, by hydroxyl, by alkoxy having 1–4 C atoms, in particular methoxy, or by trifluoromethyl.

As used herein, the substituent —NH—C(O)—($C_1$–$C_6$-alkyl) is defined as an amide wherein $C_1$–$C_6$-alkyl is a straight- or branched-chain alkyl having 1 to 6 C atoms, preferably having 1 to 4 C atoms, e.g. methyl, ethyl, i-propyl, tert-butyl and hexyl.

As used herein, 'stereoisomer' or 'stereoisomeric form' is a general term used for all isomers of individual molecules that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers).

As used herein, 'R' and 'S' are used as commonly used in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counterclockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determining) group is on the right side of the carbon at the chiral center and 'L', that of the isomer in which it is on the left.

As used herein, "halogen" or "halo" means fluorine, chlorine, bromine and iodine.

As used herein, 'treat' or 'treating' means any treatment, including but not limited to, alleviating symptoms, eliminating the causation of the symptoms either on a temporary or permanent basis, or to preventing or slowing the appearance of symptoms and progression of the named disease, disorder or condition.

As described herein, the term 'patient' refers to a warm blooded animal such as a mammal which is afflicted with a particular disease, disorder or condition. It is explicitly understood that guinea pigs, dogs, cats, rats, mice, horses, cattle, sheep, and humans are examples of animals within the scope of the meaning of the term.

As used herein, 'disease' refers to an illness, sickness or an interruption, cessation or disorder of body functions, systems or organs.

As used herein, 'disorder' refers to a disturbance of function, structure or both resulting from a genetic or embryologic failure in development, or from exogenous factors such as poison, injury or disease.

As used herein, 'prophylaxis' refers to the prevention of disease.

As used herein, 'pharmaceutical carrier' refers to known pharmaceutical excipients useful in formulating pharmaceutically active compounds for administration, and which are substantially nontoxic and nonsensitizing under conditions of use. The exact proportion of these excipients is determined by the solubility and chemical properties of the active compound, the chosen route of administration as well as standard pharmaceutical practice.

As used in the examples and preparations the terms used therein shall ha the meanings indicated as follows: Me (methyl), Et (ethyl), Ph (phony!), $Et_3N$ (triethylamine), DMF (dimethylformamide), DMSO (dimethylsulfoxide), rt (room temperature), min or mim. (minutes), h (hours), UV (ultraviolet), LC-MS (liquid chromatography mass spectrometry), t-Boc or Boc (tert-butoxycarbonyl), TFA (trifluoro acetic acid). HOAc (acetic acid), EtOAc (ethyl acetate), g (gram), mg (milligram), $\mu$g (microgram), ng (nanogram), mL (milliliter), $\mu$L (microliter), L (liter); HPLC (high-performance liquid chromatography), TLC layer chromatography); rpm (revolutions per minute), g/L (grams per liter), L/min (liters per minute), mL/min (milliliters per minute), M (molar), mM (millimolar), $\mu$M (micromolar), $\mu$Ci (microCurie), CPM (counts per minute), mm (millimeter), $\mu$ (micron), nm (nanometer), ° C. (degrees Celsius), and K (Kelvin).

The invention preferably relates to a compound of the formula (I), wherein R is H or a group of the formula —(CH($OR^2$))$_5$—$CH_2$—$OR^2$, $R^1$ and $R^2$ are independently H or $C_1$–$C_6$-alkyl, or a stereoisomeric form and/or a pharmaceutically acceptable salt thereof.

The invention more preferably relates to a compound of the formula (I), wherein R is a group of the formula —(CH($OR^2$))$_5$—$CH_2$—$OR^2$, and $R^1$ and $R^2$ are H, or a stereoisomeric form and/or a pharmaceutically acceptable salt thereof. Such a compound is described by formula (II):

(II)

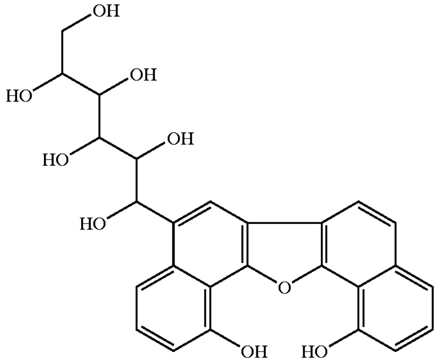

A further embodiment of the invention is a compound of the formula (I), wherein R and $R^1$ are H, or a pharmaceutically acceptable salt thereof. Such a compound is described by formula. (III):

(III)

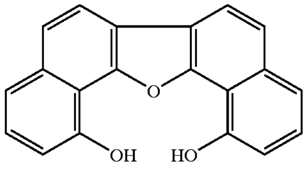

Chiral centers in the compounds of the formulae (I) and (II) can be present, if not stated otherwise, in the R or in the S configuration. The invention relates both to the optically pure compounds and to mixtures of stereoisomers, such as mixtures of enantiomers and mixtures of diastereomers, in any ratio.

The invention furthermore relates to obvious chemical equivalents of the compounds of the formula (I), (II) or (III).

Obvious chemical equivalents of the compounds according to the invention are compounds which have the same activity as the compounds according to the invention and exhibit a slight chemical difference or are converted into the compounds according to the invention under mild conditions. Obvious chemical equivalents include, for example, ethers, esters, reduction products and complexes of the compounds according to the invention.

For example, one or more hydroxyl groups of the compounds of the formula (I), (II) or (III) can be etherified, for example with a $C_1$–$C_6$-alcohol by addition of acid, or esterified with an activated acid, for example, acid chlorides or other activated acid derivatives. It is further possible, for example, for one or more double bonds of the compound of the formula (I), (II) or (III) to be reduced using a suitable reductant, for example, $H_2$/Pd.

The phenol groups of the compounds according to the invention can furthermore form chelates with mono- or polyvalent cations. Compounds which contain chelate-forming phenol groups moreover have an antioxidant effect (N. Sugihara et al., Journal of Health Science 2001, 47(2), 99–106). Antioxidants (oxidation inhibitors) are organic compounds which inhibit or prevent undesired changes in the substances to be protected caused by the effects of oxygen. Antioxidants are needed, for example, in plastics for protection against aging, in fats for protection against rancidity, in oils against resinification, in aromatic substances against deterioration in odor, in foodstuffs, in pharmaceuticals, etc. The action of the antioxidants is usually that they act as radical scavengers for the free radicals occurring in the oxidation. The compounds of the formulae (I), (II) and (III) can therefore also be used as chelating agents and as antioxidants.

The abovementioned methods for derivatization are described in textbooks such as Jerry March, Advanced Organic Chemistry, John Wiley & Sons, 4$^{th}$ Edition, 1992. In order to carry out derivatization reactions selectively, it can be advantageous to introduce suitable protective groups in a manner well known to one skilled in the art before the derivatization reaction. The protective groups are removed after the derivatization reaction by methods well known to one skilled in the art, and then the reaction product is purified.

The compounds of the formulae (I), (II) and (III), and the obvious chemical equivalents thereof, can be converted into the corresponding pharmaceutically acceptable salts according to methods well known to one skilled in the art.

Pharmaceutically acceptable salts of the compounds according to the invention are understood as meaning both inorganic and organic salts, such as are described in Remingtons Pharmaceutical Sciences (17th edition, page 1418 [1985]). Possible salts are, in particular, alkali metal, ammonium and alkaline earth metal salts, salts with pharmaceutically acceptable amines, and salts with inorganic or organic acids such as, for example, HCl, HBr, $H_2SO_4$, maleic acid, and fumaric acid.

The invention additionally relates to a compound of the molecular formula $C_{26}H_{24}O_9$, characterized by the $^1$H-NMR and $^{13}$C-NMR data according to table 2 (vide infra), or a stereoisomeric form and/or a pharmaceutically acceptable salt thereof.

The invention additionally relates to a compound of the molecular formula $C_{20}H_{12}O_3$, characterized by the $^1$H-NMR and $^{13}$C-NMR data according to table 3 (vide infra), or a pharmaceutically acceptable salt thereof.

The invention additionally relates to a compound of the formula (II), obtainable by fermentation of ST 003360 (DSM 14093) or of a variant and/or mutants of ST 003360 (DSM 14093) in a culture medium until the compound of the formula (II) accumulates in the culture broth, subsequent isolation of the compound of the formula (II), and, optionally, conversion into a pharmaceutically acceptable salt thereof.

The invention additionally relates to a compound of the formula (III), obtainable by fermentation of ST 004112 (DSM 14524) or of a variant and/or mutants of ST 004112 (DSM 14524) in a culture medium until the compound of the formula (III) accumulates in the culture medium, subsequent isolation of the compound of the formula (III), and, optionally, conversion into a pharmaceutically acceptable salt thereof.

The invention moreover relates to a compound of the formula (I), obtainable by fermentation of ST 003360 (DSM 14093) or of a variant and/or mutants of ST 003360 (DSM 14093) in a culture medium until the compound of the formula (II) accumulates in the culture broth, subsequent isolation of the compound of the formula (II), or fermentation of ST 004112 (DSM 14524) or of a variant and/or mutants of ST 004112 (DSM 14524) in a culture medium until the compound of the formula (III) accumulates in the culture medium, subsequent isolation of the compound of the formula (III), and subsequent conversion of a compound of formula 11 or formula III into a compound of the formula (I), and, optionally, conversion into a pharmaceutically acceptable salt thereof.

An isolate of *Drechslera australiensis*, ST 003360, was deposited in the Deutsche Sammlung von Mikroorganismen und Zellkulturen (German Collection of Microorganisms and Cell Cultures) GmbH (DSM), Mascheroder Weg 1B, 38124 Brunswick, Germany according to the rules of the Budapest convention on the 28.02.2001 under the following number: DSM 14093.

The strain *Drechslera australiensis*, ST 003360, DSM 14093, has a dark black-brown mycelium and has no further characteristic features.

An isolate of a hitherto taxonomically undetermined fungus, ST 004112, was deposited in the Deutsche Sammlung von Mikroorganismen und Zellkulturen GmbH (DSM), Mascheroder Weg 1B, 38124 Brunswick, Germany according to the rules of the Budapest convention under the following number: DSM 14524.

The strain ST 004112, DSM 14524, is gray to black on malt agar. The strain was isolated from a soil sample from French Guyana.

The invention furthermore relates to a process for the preparation of the compound of formula (II), which comprises culturing the microorganism ST 003360 (DSM 14093) or a variant and/or mutant of ST 003360 (DSM 14093) in an aqueous nutrient medium, isolating and purifying a compound of formula (II), and optionally converting it into an obvious chemical equivalent and/or a pharmaceutically acceptable salt thereof.

The invention furthermore relates to a process for the preparation of the compound of formula (III), which comprises culturing the microorganism ST 004112 (DSM 14524) or a variant and/or mutant of ST 004112 (DSM 14524) in an aqueous nutrient medium, isolating and purifying a compound of formula (III), and optionally converting it into an obvious chemical equivalent and/or a pharmaceutically acceptable salt thereof.

The invention furthermore relates to a process for the preparation of a compound of formula (I), which comprises a) culturing the microorganism ST 003360 (DSM 14093) or a variant and/or mutants of ST 003360 (DSM 14093) in an aqueous culture medium, and isolating and purifying the compound of formula (II), or culturing the microorganism ST 004112 (DSM 14524) or a variant and/or mutants of ST 004112 (DSM 14524) in a culture medium, and isolating and purifying the compound of formula (III), and b) converting a compound of formula (II) or a compound of formula (III) into a compound of formula (I), and c) optionally converting the compound of formula (I) into a pharmaceutically acceptable salt thereof.

Instead of the strain *Drechslera australiensis* ST 003360, DSM 14093, or the strain ST 004112, DSM 14524, their respective mutants and/or variants can also be employed. A mutant is a microorganism in which one or more genes of the genome have been modified, the gene or the genes being functionally and hereditarily retained which are responsible for the capability of the organism to produce the inventive compound.

Such mutants can be produced in a manner well known to one skilled in the art by physical means, for example irradiation, such as using ultraviolet rays or X-rays, or chemical mutagens, such as, for example, ethyl methanesulfonate (EMS); 2-hydroxy-4-methoxy-benzophenone (MOB) or N-methyl-N'-nitro-N-nitrosoguanidine (MNNG), or as described by Brock et al. in "Biology of Microorganisms", Prentice Hall, pages 238–247 (1994).

A variant is a phenotype of the microorganism. The microorganisms have the ability to adapt to their environment and therefore show marked physiological flexibility. In the phenotypic adaptation, cells of the microorganism are involved, the nature of the modification not being genetically conditioned and being reversible under modified conditions (H. Stolp, Microbial ecology: organisms, habitats, activities. Cambridge University Press, Cambridge, GB, page 180, 1988).

The screening for mutants and variants which produce the compounds according to the invention can be carried out by determination of the biological activity of the active compound accumulated in the culture broth, for example, by determination of the JNK-3- or hCK1ε-inhibiting action by methods well known to one skilled in the art, or by detection of such compounds, which are known as JNK-3- or hCK1ε-inhibitors, in the fermentation broth by, for example, HPLC or LC-MS methods that are well known to one skilled in the art.

The fermentation course and the formation of the compounds according to the invention can be monitored according to methods well known to one skilled in the art, such as, for example, by testing the biological activity in bioassays or by chromatographic methods such as thin-layer chromatography (TLC) or high-performance liquid chromatography (HPLC).

In a nutrient medium which contains at least one carbon and nitrogen source and also the appropriate inorganic salts, under aerobic conditions the strain *Drechslera australiensis*, ST 003360, DSM 14093, produces the compound of formula (II) according to the invention, and the strain ST 004112, DSM 14542, produces the compound of formula (III) according to the invention.

The fermentation conditions described below apply to the strain *Drechslera australiensis*, ST 003360, DSM 14093, and to the strain ST 004112, DSM 14524.

Suitable preferred carbon sources for the aerobic fermentation are assimilable carbohydrates and sugar alcohols, such as glucose, lactose, sucrose or D-mannitol, and carbohydrate-containing natural products, such as, for example, malt extract. Suitable nitrogen-containing nutrients are amino acids, peptides and proteins and their degradation products, such as peptones or tryptones, furthermore meat extracts, yeast extracts, ground seeds, for example corn, wheat, beans, soy or cotton, distillation residues from alcohol production, meat meals or yeast extracts, and also ammonium salts and nitrates. Inorganic salts which the nutrient solution can contain are, for example, chlorides, carbonates, sulfates or phosphates of the alkali metals or alkaline earth metals, iron, zinc, cobalt and manganese. Trace elements which the nutrient solution can contain are, for example, molybdenum, copper, nickel or selenium.

The formation of the compound (II) according to the invention proceeds particularly well in a nutrient solution which contains from about 0.1% to about 5%, preferably from about 0.5% to about 2%, of potato dextrose and from about 0.2% to about 5%, preferably from about 0.5% to about 1%, of yeast extract. The percent composition in each case is based on the weight of the entire nutrient solution.

The formation of the compound (III) according to the invention proceeds particularly well in a nutrient solution which contains from about 0.1% to about 5%, preferably from about 0.5% to about 2%, of malt extract and from about 0.2% to about 5%, preferably from about 0.5% to about 1%, of yeast extract. The percent composition in each case is based on the weight of the entire nutrient solution.

The culturing of the microorganism is carried out aerobically, i.e., for example, submersed with shaking and stirring in shaker flasks or fermenters, optionally with introduction of air or oxygen, or on solid media. Culturing can be carried out over a temperature range from about 18° C. to about 35° C., preferably from about 20° C. to about 30° C., in particular from about 22° C. to about 28° C. The pH range should be between from about pH 4 to about pH 8, preferably between from about pH 5 to about pH 6. The microorganism is cultured under these conditions, in general, over a period of from about 24 hours to about 300 hours, preferably from about 36 hours to about 168 hours.

Culturing is advantageously carried out in a number of stages, i.e., one or more precultures are first prepared in a liquid nutrient medium, which are then inoculated into the actual production medium, the main culture, for example in a volume ratio from about 1:10 to about 1:100. The preculture is obtained, for example, by inoculating a mycelium into a nutrient medium and allowing it to grow from about 36 hours to about 120 hours, preferably from about 48 hours to about 72 hours. The mycelium can be obtained, for example, by allowing the strain to grow from about 3 days to about 40 days, preferably from about 4 days to about 10 days, on a solid or liquid nutrient medium, for example, malt-yeast agar or potato dextrose agar. The invention is illustrated further by the following examples. Percentage compositions relate to the weight. Mixing ratios in the case of liquids relate to the volume, if no other details have been given.

The inventive compounds occur both in the mycelium and in the culture filtrate. It is therefore expedient to separate the fermentation solution into the culture filtrate and the mycelium by filtration and to dry them separately. The dried culture filtrate and the dried mycelium are expediently separately extracted using an organic solvent, for example methanol or propan-2-ol.

If a culture has been applied to solid medium, the inventive compounds are present both in the mycelium and in the solid agar medium. The entire culture is expediently lyophilized by methods well known to one skilled in the art and the lyophilizate is extracted with an organic solvent, for example methanol or propan-2-ol.

The extraction can be carried out over a wide pH range, but it is expedient to work in a neutral or weakly alkaline medium, preferably between from about pH 7 to about pH 10. The extract can be concentrated and dried, for example, in vacuo.

One method of isolation is by separation using different polarities in a manner well known to one skilled in the art.

A further method of purification is chromatography on adsorption resins such as, for example, on Diaion® HP-20 (Mitsubishi Casei Corp., Tokyo), on Amberlite® XAD 7 (Rohm and Haas, USA), on Amberchrom® CG, (Toso Haas, Philadelphia, USA) or on the like. Also suitable are numerous reversed-phase supports, e.g. $RP_8$ and $RP_{18}$, such as have become generally well known to one skilled in the art, for example, in the context of high-pressure liquid chromatography (HPLC).

A further possibility for purification of the compounds according to the invention consists in the use of "normal-phase" chromatographic supports, such as, for example, silica gel or $Al_2O_3$ or others in a manner well known to one skilled in the art.

An alternative isolation process is the use of molecular sieves, such as, for example, Fractogel® TSK HW-40 (Merck, Germany) and others, in a manner well known to one skilled in the art. It is moreover possible to recover the compounds according to the invention from enriched material by crystallization. Suitable solvents for this purpose are, for example, organic solvents and their mixtures, wherein the solvents may be anhydrous or water may be added. An additional process for the isolation and purification of the compounds according to the invention consists in the use of anion exchangers, preferably in the pH range from about pH 4 to about pH 10. Particularly suitable for this purpose is the use of buffer solutions to which portions of organic solvents have been added.

It has surprisingly been found that the compounds of formula (I) according to the invention are inhibitors of JNK-3 and CK-1. Table 1 summarises the activity data of the inventive compounds by way of example:

TABLE 1

Activity data for the compounds of formula (II) and (III)

| Enzyme | Compound II $IC_{50}$ ($\mu$M) | Compound III $IC_{50}$ ($\mu$M) |
|---|---|---|
| JNK-3 | 1.1 | 2.8 |
| hCK1$\epsilon$ | 2.9 | not determined |

The present invention therefore also relates to the use of one or more of the compounds of the formula (I). (II) or (Ill) according to the invention for the treatment and/or for the prophylaxis of degenerative neuropathies, far example Alzheimer's disease, or psychiatric disorders, for example depression, sleep disturbances or seasonal affective disorder.

The present invention additionally relates to a pharmaceutical composition containing one or more compounds according to the invention.

Said pharmaceutical composition containing a compound of the formula (I), (II) and/or (III) is prepared by using one or more pharmaceutically acceptable excipients and the mixture is formed into a pharmaceutical composition suitable for administration by methods well known to one skilled in the art.

The pharmaceutical compositions according to the invention can be administered enterally (orally), parenterally (intramuscularly or intravenously), rectally or locally (topically). Said pharmaceutical compositions can be administered in the form of solutions, powders, tablets, capsules including microcapsules, ointments, creams, gels or suppositories. Possible pharmaceutically acceptable excipients for formulations of this type are the pharmaceutically acceptable liquid or solid fillers and extenders, solvents, emulsifiers, lubricants, flavoring agents, colorants and/or buffer substances. As a suitable dose, from about 0.1 mg/kg to about 1000 mg/kg, preferably from about 0.2 mg/kg to about 100 mg/kg of body weight are administered in dosage units which contain at least the effective daily amount of the compounds according to the invention, e.g. from about 30 mg to about 3000 mg, preferably from about 50 mg to about 1000 mg.

EXPERIMENTAL

The following examples are intended to serve for the illustration of the invention in greater detail, without restricting the breadth of the invention in any manner.

Example 1

Preparation of a Glycerol Culture of *Drechslera australiensis* ST 003360, DSM 14093.

A sterile 300 mL Erlenmeyer flask containing 100 mL of nutrient solution (malt extract 2.0%, yeast extract 0.2%, glucose 1.0%, $(NH_4)_2HPO_4$ 0.05%, pH 6.0) was inoculated with the strain *Drechslera australiensis*, ST 003360, DSM 14093, and incubated on a rotating shaker for 7 days at 25° C. and 140 rpm. A 1.5 mL sample of this culture was then diluted with 2.5 mL of 50% glycerol and stored at −135° C.

Example 2

Preparation of a Main Culture in the Erlenmeyer Flask of *Drechslera australiensis*, ST 003360, DSM 14093.

A sterile 300 mL Erlenmeyer flask containing 100 mL of nutrient solution (2.4 g/L of potato dextrose, 0.2 g/L of yeast extract) was inoculated with a culture grown in a slant tube (same nutrient solution, but with 2% agar) or with 1 mL of a glycerol culture as prepared in example 1. The culture was incubated at 180 rpm and 25° C. on a shaker. The maximum production of the drechsleranol compound of formula (II) according to the invention was achieved after about 144 hours. For inoculation of 10 L fermenters, a 48 to 96 hour-old submersed culture (inoculation amount about 10%) from the same nutrient solution sufficed.

Example 3

Preparation of the Compound of the Formula (II) in a 10 L Fermenter

A 10 L fermenter was operated under the following conditions:

Nutrient Medium
2.4 g/L of potato dextrose
0.2 g/L of yeast extract
pH 5.1 (before sterilisation)

| | |
|---|---|
| Incubation time: | 115 hours |
| Incubation temperature: | 25° C. |
| Stirrer speed: | 200 rpm |
| Aeration: | 15 L/min |

It was possible to suppress foam formation by repeated addition of ethanolic polyol solution. The production maximum was achieved after about 96 hours to about 144 hours.

Example 4

Isolation of the Compound of Formula (II)

A fermentation batch from a glass fermenter having a nominal volume of 10 L was lyophilized and extracted three times with 3 L of methanol in each case. The methanol extract was reduced to about 500 mL in vacuo and diluted with water to a methanol content of 10%. The diluted extract (5 L) was then applied to a prepared glass column (BPG 100, 4 L internal volume, Pharmacia Biotech), which was packed with about 0.5 liter of MCI-Gel® CHP-20P material (adsorber resin from Mitsubishi Chemicals, Japan). The column was then eluted using a gradient of 100% water to 100% acetonitrile in 60 min. The column flow (50 mL/min) was collected in fractions (50 mL each). All fractions were tested in the JNK-3 assay and the active fractions (fractions 26–44) were combined. Concentration in vacuo and subsequent lyophilization afforded 1.21 g of a brown powder.

This powder was applied to a LUNA® 10μ C18 (2) column (size: 50 mm×250 mm; Phenomenex, Germany) with a LUNA® 10μ C18 (2) precolumn (size: 21.2 mm×60 mm) and chromatographed using a gradient of 0% to 50% acetonitrile in 0.1% ammonium acetate/water over the course of 50 minutes. The flow of the eluent was 125 mL/min, the fraction size 250 mL. Fraction 17 showed the greatest activity in the bioassay. Fraction 17 was lyophilized (220 mg) and subsequently investigated by means of analytical HPLC and mass spectrometry which showed that the fraction consisted of a single substance (purity>95%).

Example 5

Characterisation of the Compound of Formula (II)

(II)

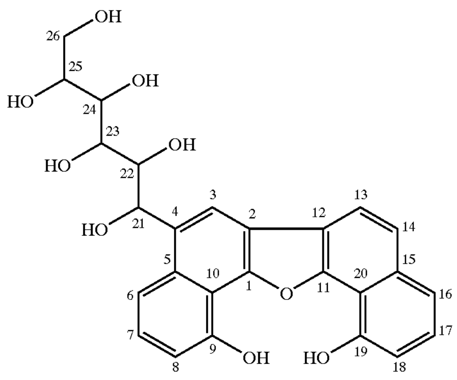

The physicochemical and spectroscopic properties of the compound isolated according to example 4 are summarised as follows:

Molecular formula: $C_{26}H_{24}O_9$

Molecular weight: 480

UV maxima: 226, 236, 260, 312, 340 nm $^1H$- and $^{13}C$-NMR: see table 2

TABLE 2

$^1H$- and $^{13}C$ NMR chemical shifts δ (ppm) of the compound of formula (II) in DMSO-$d_6$ (TMS) at 300 K.

| Position | $^1H$ (δ, ppm) | $^{13}C$ (δ, ppm) |
|---|---|---|
| 1 | — | 152.57 |
| 2 | — | 118.06 |
| 3 | 7.45 | 129.9 (broad) |
| 4 | — | 124.95 |
| 5 | — | 134.57 |
| 6 | 7.62 | 115.83 |
| 7 | 7.26 | 125.99 |
| 8 | 6.75 | 107.91 |
| 9 | — | 154.76 |
| 10 | — | 115.27 |
| 11 | — | 152.27 |
| 12 | — | 119.16 |
| 13 | 7.38 | 130.13 |
| 14 | 7.30 | 117.58 |
| 15 | — | 135.66 |
| 16 | 7.28 | 118.72 |
| 17 | 7.25 | 126.37 |
| 18 | 6.75 | 108.19 |
| 19 | — | 154.50 |
| 20 | — | 115.15 |
| 21 | 4.62 | 78.4 (broad) |
| 22 | 3.62 | 73.43 |
| 23 | 3.39 | 78.91 |
| 24 | 3.25 | 70.47 |
| 25 | 3.34 | 81.29 |
| 26 | 3.69, 3.45 | 61.37 |

Example 6

Preparation of a Glycerol Culture of ST 004112, DSM 14524

A sterile 300 mL Erlenmeyer flask containing 100 mL of nutrient solution (malt extract 2.0%, yeast extract 0.2%, glucose 1.0%, $(NH_4)_2HPO_4$ 0.05%, pH 6.0) was inoculated with the strain DSM 14524 and incubated on a rotating shaker for 7 days at 25° C. and 140 rpm. A 1.5 mL sample of this culture was then diluted with 2.5 mL of 50% glycerol and stored at −135° C.

Example 7

Preparation of a Main Culture of ST 004112, DSM 14524, on Solid Medium (Plates)

Fifty sterile 25×25 cm plates were poured using 200 mL of a nutrient solution containing 20 g/L of malt extract, 2 g/L of yeast extract and 2% agar and having a pH of 7.0 in each case. The plates were inoculated with 2 mL of a preculture from example 6 and incubated at 25° C. The maximum production of the compound of the formula (III) was achieved after about 360 hours.

Example 8

Preparation of a Main Culture in the Erlenmeyer Flask of ST 004112, DSM 14524

A sterile 300 mL Erlenmeyer flask containing 100 mL of nutrient solution (2.4 g/L of potato dextrose, 0.2 g/L of yeast extract) was inoculated with a culture grown in a slant tube (same nutrient solution, but with 2% agar) or with 1 mL of a glycerol culture (see example 6) and incubated at 180 rpm and 25° C. on a shaker. The maximum production of the compound of the formula (III) was achieved after about 144 hours. For the inoculation of 10 L fermenters, a 48 hour- to 96 hour-old submersed culture (inoculation amount about 10%) of the same nutrient solution sufficed.

Example 9

Isolation of the Compound of Formula (III)

Fifty plate cultures (20×20 cm each plate) were lyophilized and extracted twice with 10 L of methanol in each case. The methanol extract was reduced to about 500 mL in vacuo and diluted to a methanol content of 10% with water. The diluted extract (5 L) was then applied to a prepared glass column (BPG 100, 4 L internal volume, Pharmacia Biotech), which was packed with about 0.5 liter of MCI-Gel® CHP-20P material (adsorber resin of Mitsubishi Chemicals, Japan). The column was eluted using a gradient of 100% water to 100% acetonitrile over 30 min. The column flow (50 mL/min) was collected in fractions (50 mL each). All fractions were tested in the JNK-3 assay and the active fractions (fractions 30–44) were combined. Concentration in vacuo and subsequent lyophilization afforded a brown gummy residue.

The residue was dissolved in water/acetonitrile (1:1), centrifuged and applied to a LUNA® 10 μC18 (2) column (size: 21 mm×250 mm; Phenomenex, Germany) and chromatographed using a gradient of 0% to 100% acetonitrile in 0.1% ammonium acetate/water over the course of 60 minutes. The flow of the eluent was 33 mL/min the fraction size 33 mL. Fractions 28–32 showed the greatest activity in the bioassay. Fractions 28–32 were lyophilized and then further purified. For this, the substance was chromatographed on a LUNA® 5 μC18 (2) column (size: 10 mm×250 mm; Phenomenex, Germany) using a gradient of 30% to 60% acetonitrile in 0.1% ammonium acetate/water over the course of 45 minutes. The flow of the eluent was 6.5 mL/min, and the fraction size was 6.5 mL. Fractions 18–24 showed the greatest activity in the bioassay. After freeze-drying (yield: 10 mg), subsequent analysis by means of analytical HPLC and MS spectrometry showed that the material was a homogeneous compound (purity>95%).

Example 10

Characterisation of the Compound of Formula (III)

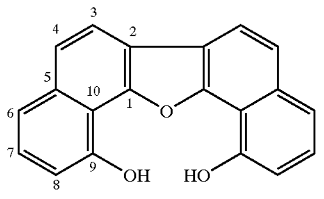

(III)

The physicochemical and spectroscopic properties of the compound isolated according to example 9 can be summarised as follows:

Molecular formula: $C_{20}H_{12}O_3$

Molecular weight: 300

UV maxima: 226, 236, 260, 312, 340 nm $^1H$- and $^{13}C$-NMR: see table 3

TABLE 3

$^1H$- and $^{13}C$ NMR chemical shifts δ (ppm) of the compound of formula (III) in $CD_3OD$ (TMS) at 300 K.

| Position | $^1H$ (δ, ppm) | $^{13}C$ (δ, ppm) |
|---|---|---|
| 1 | — | ~154.3 (a) |
| 2 | — | ~121.3 (a) |
| 3 | 7.46 | 130.63 |
| 4 | 7.31 | 119.55 |
| 5 | — | 137.60 |
| 6 | 7.24 | 119.55 |
| 7 | 7.22 | 127.52 |
| 8 | 6.69 | 109.20 |
| 9 | — | ~157.0 |
| 10 | — | ~117.5 (a) |

(a) For these carbon atoms, no (or an extremely broad) signal is observed in the $^{13}C$ spectrum. The chemical shifts were therefore determined by means of correlations in the Heteronuclear Multi-Bond Connectivity (HMBC) spectrum.

Example 11

Activity of the Compounds of Formulae (II) and (III) in the JNK-3 Assay

The assay is carried out on a CyBio pipetter system in a 384-hole plate format. The assay contains 10 μL of sample (extract or pure substance, for example a compound of formula (II) or of formula (III)) in 3% DMSO, 10 μL of an enzyme/substrate mixture (JNK-3/GST-ATF2) and 10 μL of ATP in a final volume of 30 μL. After incubation at 37° C. for 20 minutes, 50 μL of the HTRF antibody mixture (XL665-anti-GST/(Eu)cryptate anti-P-ATF2) are added. After 120 minutes at room temperature, the signal emission of the energy transfer and of europium at 665 and 615 nm is measured after the samples have been stimulated at 340 nm in a Victor² (WALLAC).

Buffer I for the Dilution of JNK3, GST-ATF2, ATP:

| | |
|---|---|
| 25 mM | HEPES, pH 7.5 |
| 100 μM | $MgCl_2$ |
| 0.03% | TRITON X 100 |
| 10 mM | DTT |
| 5% | Glycerol |

Buffer II for the Dilution of the HTRF Reagents:

| | |
|---|---|
| 100 mM | HEPES, pH 7.0 |
| 100 mM | KF |
| 133 mM | EDTA |
| 1 g/L | BSA |

| Reagents: | Supplier: | Final concentration: |
|---|---|---|
| JNK3 Kinase | Biotech, Vitry | 8 ng/well |
| GST-ATF2 | Biotech, Vitry | 88 ng/well |
| ATP | Sigma, A7699 | 15 μM |
| Anti-GST-XL665 | CisBio | 125 ng/well |
| Anti-P-ATF2-(Eu)cryptate | NEB/CisBio | 6 ng/well |

Each plate contains 16 positive controls (maximum energy transfer, buffer I instead of samples), 8 blank controls (minimum energy transfer, buffer II instead of ATP) and 8 holes which contain EDTA 200 μM.

The results are calculated as follows:

Firstly, the signal ratio=(intensity (665 nm)/intensity (615 nm)) is determined. A blank correction is then made using the following formula:

$$\text{delta } F(\%)=[(\text{ratio (sample)}-\text{ratio(minimum)})/(\text{ratio (minimum)})]\times 100$$

The activity of the samples is then calculated in the following manner:

$$\text{Inhibition }(\%)=100\times[1-(\text{delta } F(\text{sample})/\text{delta } F(\text{maximum}))]$$

Example 12

Activity of the Compound of Formula (II) in the hCK1ε Assay

The assay is carried out in a Jobi-Well (CyBio) and Biomek 2000 pipetter system in the 384-hole plate format. The 384-hole plates are coated with 50 μL per well of a casein solution of the concentration 100 μg/mL in coating buffer (corresponds to 5 μg of casein per well, casein Sigma) and stored overnight at 4° C. Washing four times with 90 μL of wash solution 1 (50 mM HEPES pH 7.4 and 150 mM NaCl) is then carried out. The reaction is carried out in a final volume of 50 μL. During the course of this, 10 μL of dilute natural substance extract in each case, for example a compound of formula (II) or a compound of formula (III), 20 μL of hCK1ε enzyme solution (corresponds to 29 ng of casein per well) and 20 μL of ATP solution (final concentration: 0.4 μCi of $^{33}$P-γ-ATP radiolabeled ("hot") and 0.4 μM of cold ATP per well) are pipetted onto the coated plates. The plates are then incubated at 37° C. for one hour. The plates are then washed four times with 75 μL of wash solution 2 (phosphoric acid, 3%) and measured for 30 seconds in a MicroBeta Trilux counter (WALLAC).

hCK1ε Enzyme Solution: 1.45 μg of Recombinant hCK1ε per mL of Kinase Buffer

Kinase Buffer

50 M HEPES pH 7.4
10 mM $MgCl_2$
0.25 mM DTT
0.6 mM EGTA

Coating Buffer:

27.5 mM $Na_2CO_3$
22.5 mM $NaHCO_3$ (pH 9.6)
in 0.9% NaCl

ATP Solution: 20 μCi/mL of $^{33}$P-γ-ATP and 1 μM of Cold ATP

On each plate, 16 holes are used in order to determine the total enzyme activity (without inhibitor addition) and a further 16 holes without enzyme addition in order to determine the nonspecific reaction.

The inhibition of a sample can be calculated according to the following formula:

$$[1-(CPM(\text{sample})-CPM(\text{nonspec.}))/(CPM(\text{enzyme concentration})-CPM(\text{nonspec.}))]\times 100(\%)$$

The results of the JNK-3 and hCK1ε assays are summarized in table 1 (vide supra).

What is claimed is:

1. A compound of formula (I)

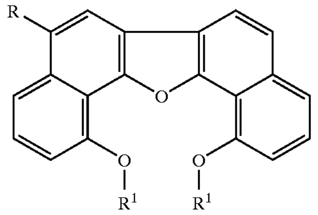

(I)

wherein:

R is H, or a group of the formula —(CH(OR$^2$))$_5$—CH$_2$—OR$^2$;

$R^1$ and $R^2$ independently are H, $C_1$–$C_6$-alkyl, $C_2$–$C_6$-alkenyl, $C_2$–$C_6$-alkenyl or $C_{6-C10}$-aryl, wherein said $C_1$–$C_6$-alkyl, $C_2$–$C_6$-alkenyl, $C_2$–$C_6$-alkynyl or $C_6$–$C_{10}$-aryl are optionally mono- or disubstituted by —OH, =O, —O—$C_1$–$C_6$-alkyl, —O—$C_2$–$C_6$-alkenyl, $C_6$–$C_{10}$-aryl, —NH—$C_1$—$C_6$-alkyl, —NH—$C_2$–$C_6$-alkenyl, —$NH_2$ or halogen, wherein said —O—$C_1$—$C_6$-alkyl, —O—$C_2$–$C_6$-alkenyl, $C_6$–$C_{10}$ aryl, —NH—$C_1$–$C_6$-alkyl and —NH—$C_2$–$C_6$-alkenyl substituents are optionally substituted by —CN, —NH—C(O)—($C_1$–$C_6$-alkyl) or =NOH; or a stereoisomeric form thereof, or a pharmaceutically acceptable salt thereof.

2. The compound according to claim 1 wherein $R^1$ and $R^2$ independently are H or $C_1$–$C_6$-alkyl.

3. The compound according to claim 2 of formula (II)

(II)

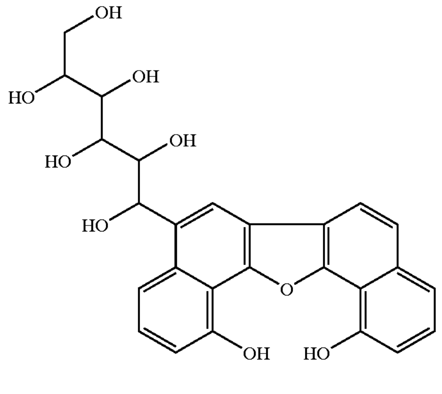

or a stereoisomeric form thereof, or a pharmaceutically acceptable salt thereof.

4. The compound of formula (II) according to claim 3 having $^1$H-NMR spectrum peaks at about 3.25. 3.34, 3.39, 3.45, 3.62, 3.69, 4.62, 6.75, 6.75, 7.25, 7.26, 7.28, 7.30, 7.38, 7.45, 7.62 ppm and $^{13}$C-NMR spectrum peaks at about 61.37, 70.47, 73.43, 78.4 (broad), 78.91, 81.29, 107,91, 108.19, 115.15, 115.27, 115.83, 117.58, 118.06, 118.72, 119.16, 124.95, 125.99, 126.37, 129.9 (broad), 130.13, 134.57, 135.66, 152.27, 152.57, 154.50, 154.76 ppm.

5. The compound according to claim 2 of formula (III)

(III)

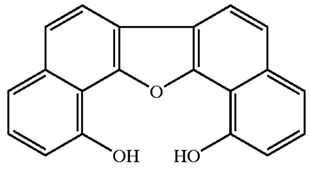

having $^1$H-NMR spectrum peaks at about 6.69, 7.22, 7.24, 7.31 7.46 ppm and $^{13}$C-NMR spectrum peaks at about 109.20, 117.5, 119.55, 119.55, 121.3, 127.52, 130.63, 137.60, 154.3, 157.0 ppm, or a pharmaceutically acceptable salt thereof.

6. A process for the preparation of the compound of formula (I) as set forth in claim 1 comprising the steps of a) culturing the microorganism ST 003360 (DSM 14093) or a variant and/or mutants of ST 003360 (DSM 14093) in a culture medium, and isolating and purifying the compound of the formula (II), or culturing the microorganism ST 004112 (DSM 14524 or a variant and/or mutants of ST 004112 (DSM 14524) in a culture medium, and isolating and purifying the compound of the formula (III), b) converting the compound of formula (II) or the compound of formula (III) into the compound of formula (I), and c) optionally converting the compound of formula (I) into a pharmaceutically acceptable salt.

7. The compound of formula (I) produced by the process of claim 6.

8. A process for the preparation of the compound of formula (II) according to claim 3 comprising the steps of a) culturing the microorganism ST 003360 (DSM 14093 or a variant and/or mutant of ST 003360 (DSM 14093), b) isolating and purifying the compound of formula (II), and c) optionally converting the compound of formula (II) into a chemical equivalent or a pharmaceutically acceptable salt.

9. The compound of formula (II) produced by the process of claim 8.

10. A process for the preparation of the compound of formula (III) according to claim 5 comprising the steps of a) culturing the microorganism ST 004112 (DSM 14524 or a variant and/or mutant of ST 004112 (DSM 14524), b) isolating and purifying the compound of formula (III), and c) optionally converting the compound of formula (III) in a chemical equivalent or a pharmaceutically acceptable salt.

11. The compound of formula (III) produced the process of claim 10.

12. A pharmaceutical composition having JNK-3 inhibitory activity comprising a pharmaceutically acceptable carrier and a therapeutically effective amount of a compound of formula (I)

(I)

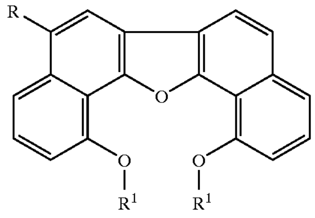

wherein:

R is H, or a group of the formula —(CH(OR$^2$))$_5$—CH$_2$—OR$^2$;

R$^1$ and R$^2$ independently are H, $C_1$–$C_6$-alkyl, $C_2$–$C_6$-alkenyl, $C_2$–$C_6$-alkynyl or $C_{6-C10}$-aryl, wherein said $C_1$–$C_6$-alkyl, $C_2$–$C_6$-alkenyl, $C_2$–$C_6$-alkynyl or $C_6$–$C_{10}$-aryl are optionally mono- or disubstituted by —OH, =O—, O—$C_1$–$C_6$-alkyl, —O—$C_2$–$C_6$-alkenyl, $C_6$–$C_{10}$-aryl, —NH—$C_1$–$C_6$-alkyl, —NH—$C_2$–$C_6$-alkenyl, —NH$_2$ or halogen, wherein said —O—$C_1$–$C_6$-alkyl, —O—$C_2$–$C_2$–$C_6$-alkenyl, $C_6$–$C_{10}$-aryl, —NH—$C_1$–$C_6$-arkyl and —NH—$C_2$–$C_6$-alkenyl substituents are optionally substituted by —CN, —NH—C(O)—($C_1$–$C_6$-alkyl) or =NOH; or a stereoisomeric form thereof, or a pharmaceutically acceptable salt thereof.

13. A pharmaceutical composition having hCK1ε inhibitory activity comprising a pharmaceutically acceptable carrier and a therapeutically effective amount of a compound of formula (I)

(I)

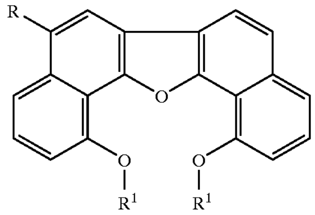

wherein:

R is H, or a group of the formula —(CH(OR$^2$))$_5$—CH$_2$—OR$^2$;

R$^1$ and R$^2$ independently are H, $C_1$–$C_6$-alkyl, $C_2$–$C_6$-alkenyl, $C_2$–$C_6$-alkynyl or $C_6$–$C_{10}$-aryl, wherein said $C_1$–$C_6$-alkyl, $C_2$–$C_6$-alkenyl, $C_2$–$C_6$-alkynyl or $C_6$–$C_{10}$-aryl are optionally mono- or disubstituted by —OH, =O, —O—$C_1$–$C_6$-alkyl, —O—$C_2$–$C_6$-alkenyl, $C_6$–$C_{10}$-aryl, —NH—$C_1$—$C_6$-alkyl, —NH—$C_2$–$C_6$-alkenyl, —$NH_2$or halogen, wherein said —O—$C_1$–$C_6$-alkyl, —O—$C_2$–$C_6$-alkenyl, $C_6$–$C_{10}$aryl, —NH—$C_1$–$C_6$-alkyl and —NH—$C_2$–$C_6$-alkenyl substituents are optionally substituted by —CN, —NH—C(O)—($C_1$–$C_6$-alkyl) or =NOH; or a stereoisomeric form thereof, or a pharmaceutically acceptable salt thereof.

14. A method of inhibiting JNK-3 activity to treat a degenerative neuropathy which comprises administering to a patient in need of said treatment a therapeutically effective amount of a compound of formula (I):

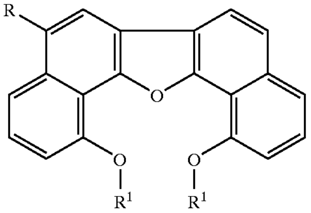

(I)

wherein:

R is H, or a group of the formula —(CH($OR^2$))$_5$—$CH_2$—$OR^2$;

$R^1$ and $R^2$ independently are H, $C_1$–$C_6$-alkyl, $C_2$–$C_6$-alkenyl, $C_2$–$C_6$-alkynyl or $C_6$–$C_{10}$-aryl, wherein said $C_1$–$C_6$-alkyl, $C_2$–$C_6$-alkenyl, $C_2$–$C_6$-alkynyl or $C_6$–$C_{10}$-aryl are optionally mono- or disubstituted by —OH, =O, —O—$C_{1-C6}$-alkyl —O—$C_2$–$C_6$-alkenyl, $C_6$–$C_{10}$-aryl, —NH—$C_1$–$C_6$-alkyl, —NH—$C_2$–$C_6$-alkenyl, —$NH_2$ or halogen, wherein said —O—$C_1$–$C_6$-alkyl, —O—$C_2$–$C_6$-alkenyl, $C_6$–$C_{10}$-aryl, —NH—$C_1$–$C_6$-alkyl and —NH—$C_2$–$C_6$-alkenyl substituents are optionally substituted by —CN, —NH—C(O)—($C_1$–$C_6$-alkyl) or =NOH; or a stereoisomeric form thereof, or a pharmaceutically acceptable salt thereof.

15. The method according to claim 14 wherein the degenerative neuropathy is Alzheimer's disease.

16. A method of inhibiting hCK1ε activity to treat a psychiatric disorder which comprises administering to patient in need of said treatment a therapeutically effective amount of a compound of formula (I):

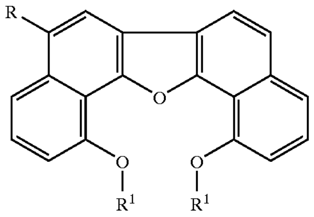

(I)

wherein:

R is H, or a group of the formula —(CH($OR^2$))$_5$—$CH_2$—$OR^2$;

$R^1$ and $R^2$ independently are H, $C_1$–$C_6$-alkyl, $C_2$–$C_6$-alkenyl, $C_2$–$C_6$-alkynyl or $C_{6-C10}$-aryl, wherein said $C_1$–$C_6$-alkyl, $C_2$–$C_6$-alkenyl, $C_2$–$C_6$-alkynyl or $C_6$–$C_{10}$-aryl are optionally mono- or disubstituted by —OH, =O, —O—$C_1$–$C_6$-alkyl, —O—$C_2$–$C_6$-alkenyl, $C_6$–$C_{10}$-aryl, —NH—$C_1$–$C_6$-alkyl, —NH—$C_2$–$C_6$-alkenyl, —NH $_2$ or halogen, wherein said —O—$C_1$–$C_6$-alkyl, —O—$C_2$–$C_6$-alkenyl, $C_6$–$C_{10}$-aryl, —NH —$C_1$–$C_6$-alkyl and —NH—$C_2$–$C_6$-alkenyl substituents are optionally substituted by —CN, —NH—C(O)—($C_1$–$C_6$-alkyl) or =NOH; or a stereoisomeric form thereof, or a pharmaceutically acceptable salt thereof.

17. The method according to claim 16 wherein the psychiatric disorder is depression, sleep disturbances or seasonal affective disorder.

18. An antioxidant composition comprising an effective amount of a compound as set forth in claim 1.

19. A mono- or polyvalent cation chelate forming composition comprising an effective amount of a compound as set forth in claim 1.

* * * * *